(12) United States Patent
Schroeppel

(10) Patent No.: US 7,073,511 B2
(45) Date of Patent: *Jul. 11, 2006

(54) APPARATUS FOR IMPARTING PHYSICIAN-DETERMINED SHAPES TO IMPLANTABLE TUBULAR DEVICES

(75) Inventor: Edward A. Schroeppel, Roswell, GA (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 134 days.

This patent is subject to a terminal disclaimer.

(21) Appl. No.: 10/142,517

(22) Filed: May 8, 2002

(65) Prior Publication Data

US 2002/0124857 A1 Sep. 12, 2002

Related U.S. Application Data

(63) Continuation of application No. 09/408,971, filed on Sep. 29, 1999, now Pat. No. 6,395,038, which is a continuation of application No. 08/914,411, filed on Aug. 19, 1997, now Pat. No. 6,024,764.

(51) Int. Cl.
*A61B 19/00* (2006.01)
(52) U.S. Cl. ................................. 128/898; 623/23.64
(58) Field of Classification Search ... 623/23.64–23.71
See application file for complete search history.

(56) References Cited

U.S. PATENT DOCUMENTS

| 3,612,038 A | 10/1971 | Halligan | 128/2.05 R |
| 3,890,977 A | 6/1975 | Wilson | 128/418 |
| 4,950,258 A | 8/1990 | Kawai et al. | 604/281 |
| 5,306,245 A | 4/1994 | Heaven | 604/95 |
| 5,571,160 A | 11/1996 | Nyman | 607/122 |
| 5,617,854 A | 4/1997 | Munsif | 128/642 |
| 5,811,043 A | 9/1998 | Horrigan et al. | 264/138 |

OTHER PUBLICATIONS

Hayashi, S..,et al. , "Properties and Applications of Polyurethane-Series Shape Memory Polymer", *Proceedings of ANTEC '94*, (1994),p. 1998-2001.

*Primary Examiner*—Thomas Barrett
(74) *Attorney, Agent, or Firm*—Schwegman, Lundberg, Woessner & Kluth, P.A.

(57) ABSTRACT

A tubular sleeve is provided for enabling a physician to impart a preselected shape in an implantable tubular device, such as a cardiac lead, a catheter or some other tubular structure. The sleeve may be deformed by the surgeon before or at the time of implantation to customize the shape of the tubular device to the particular anatomical structures to be encountered by the device. To retain the deformation imparted by the physician, the sleeve may be composed of a heat-sensitive shape-memory material or an elastomeric material provided with a plastically deformable rib.

27 Claims, 8 Drawing Sheets

APPARATUS FOR IMPARTING PHYSICIAN-DETERMINED SHAPES TO IMPLANTABLE TUBULAR DEVICES

CROSS-REFERENCE TO RELATED APPLICATIONS

This application is a Continuation of U.S. application Ser. No. 09/408,971 now U.S. Pat. No. 6,395,038 filed Sep. 29, 1999 which is a Continuation of U.S. application Ser. No. 08/914,411 filed Aug. 19, 1997 now issued as U.S. Pat. No. 6,024,764, the specifications of which are incorporated by reference.

BACKGROUND OF THE INVENTION

1. Field of the Invention

The present invention relates generally to implantable medical devices, and more particularly to an apparatus for imparting selected bends in an implantable tubular device, such as a cardiac stimulator lead or a catheter.

2. Description of the Related Art

Implantable tubular structures, such as catheters, cardiac stimulator leads, shunts, and others are presently used for a variety of diagnostic and therapeutic purposes. The particular shape indicated for a given implantable tubular structure is dictated in large part by the anticipated physiological structures that will be encountered by the structure. For example, an endocardial lead attached distally to the ventricular apex may have a relatively straight shape. However, other situations may call for a more particularly shaped implantable tubular structure. For example, cardiac stimulator leads intended for implantation in the right atrium or coronary sinus are advantageously provided with one or more pre-established permanent bends in the tubular structure to either facilitate entry of the tubular structure into an obliquely disposed passageway, such as the coronary sinus, or to enable the tubular structure to conform with and thereby engage the internal structure of the right atrium to anchor the tubular structure in a particular position.

Presently, some effort is made by medical device manufacturers to supply implantable tubular structures with preselected shapes intended to accommodate particularized physiological structures. These commercially available devices are often supplied in different lengths, and with a variety of different types of preestablished bends. The sizes and preestablished shapes of these conventional devices are typically based on some empirically determined norm for the size and shape of the average anatomical structure to be encountered by the implantable device. The disadvantage associated with using conventional off-the-shelf implantable tubular devices is that internal anatomy varies greatly among individual patients. For this reason, a cardiac stimulator lead that may fit one patient may not be suitable for another patient. For those patients whose internal anatomy differs significantly from the hypothetical norm, the use of an off-the-shelf implantable tubular device may represent a compromise that, while not necessarily life threatening, may nevertheless involve a less than optimal treatment regimen.

For example, a cardiac stimulator lead is normally implanted into the heart by passing a lead through the superior vena cava and into the right atrium. The pathway from the superior vena cava to the right atrium is relatively straight. However, the coronary sinus ostium is located approximately at a 90° angle from that straight pathway. If the lead must be implanted in the coronary sinus, the lead must negotiate the 90° turn to successfully enter the coronary sinus ostium. Examples are legion of other anatomical structures where significant changes in direction are associated with the implantation pathway.

Another conventional device incorporates a bellows joint for establishing a shape in a catheter. The capability of this system to customize an implantable tubular device is limited in several aspects. First, the types of shapes that may be imparted are normally limited to two dimensions. Second, the portion of the catheter that may be shaped is limited to the immediate vicinity of the bellows joint.

The present invention is directed to overcoming or reducing one or more of the foregoing disadvantages.

SUMMARY OF THE INVENTION

In accordance with one aspect of the present invention, an apparatus for establishing a preselected shape in an implantable tubular device is provided. The apparatus includes a sleeve composed of a heat-sensitive shape-memory material. The sleeve has an inside diameter of sufficient size such that the sleeve may be placed around the implantable tubular device at the preselected location. The sleeve may be heated above the glass transition temperature for the heat-sensitive shape-memory material, deformed to establish the preselected shape and cooled the below the glass transition temperature to harden the sleeve so that the preselected shape is retained.

In accordance with another aspect of the present invention, an apparatus for establishing a preselected shape in an implantable tubular device is provided. The apparatus includes a first sleeve having an inside diameter of sufficient size such that the first sleeve may be placed around the implantable tubular device at the preselected location. An elongated rib is coupled to the first sleeve. The elongated rib is plastically deformable so that when a bend is introduced into the first sleeve, the elongated rib retains the introduced bend.

In accordance with still another aspect of the present invention, a method of imparting a bend at a preselected location along the length of an implantable tubular device is provided. The method includes the steps of slipping a tubular sleeve over the implantable tubular device and positioning the sleeve at the preselected location. The sleeve is plastically deformed to impart the bend.

In accordance with another aspect of the present invention, an apparatus for establishing a preselected shape in an implantable tubular device is provided. The apparatus includes a sleeve that is composed of a polymeric material that hardens upon exposure to chemical, photo, or heat stimulation. The sleeve has an inside diameter of sufficient size such that the sleeve may be placed around the implantable tubular device. The sleeve may be deformed to establish the preselected shape and exposed to chemical, photo, or heat stimulation to harden the sleeve so that the preselected shape is retained.

In accordance with still another aspect of the present invention, a cardiac stimulator lead is provided. The cardiac stimulator lead includes a tubular lead body and a sleeve coupled to the exterior of the tubular lead body. The sleeve is composed of a polymeric material that hardens upon exposure to chemical, photo, or heat stimulation. The sleeve may be deformed to establish the preselected shape in the tubular lead body and exposed to chemical, photo, or heat stimulation to harden the sleeve so that the preselected shape is retained.

In accordance with yet another aspect of the present invention, an apparatus for establishing a preselected shape in an implantable tubular device is provided. The apparatus includes a sleeve that is composed of a shape memory metal coated with a biocompatible polymeric material. The sleeve has an initial inside diameter of sufficient size such that the sleeve may be placed around the implantable tubular device. The sleeve may be heated and caused to decrease in diameter to engage the outer surface of the implantable tubular device, and deformed to establish the preselected shape.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
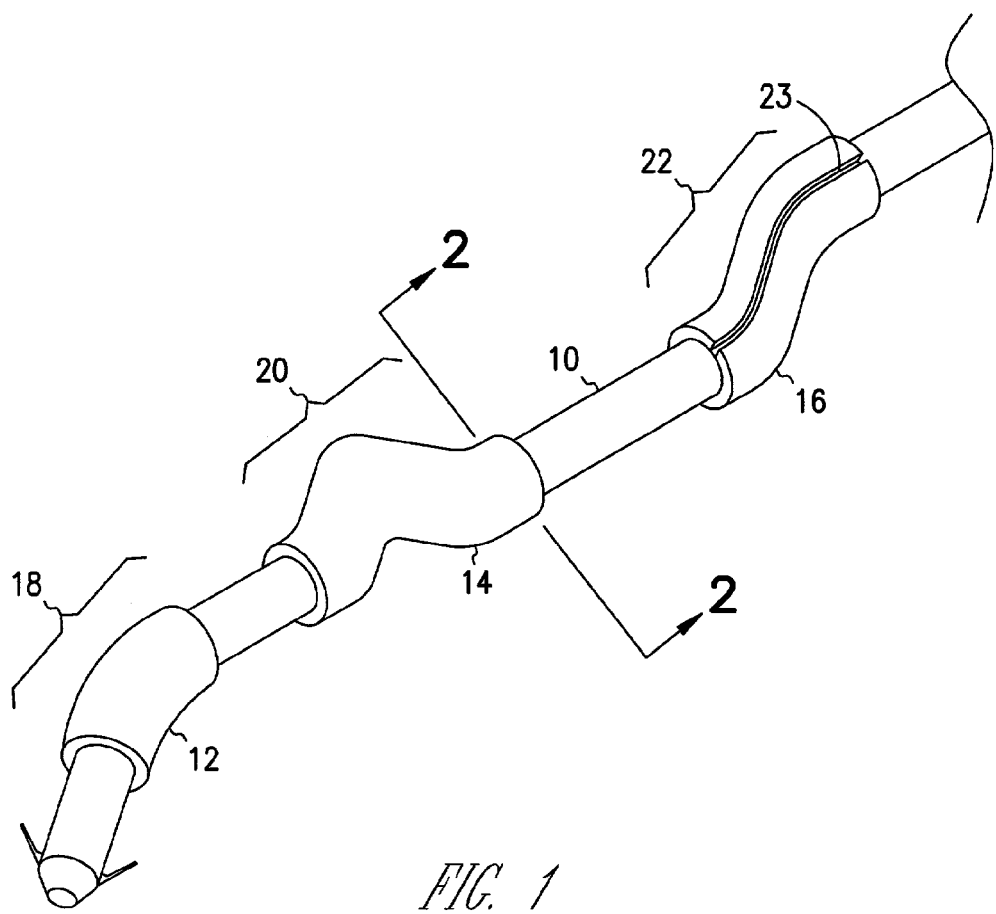
FIG. 1 is a pictorial view of a cardiac stimulator lead fitted with three sleeves in accordance with the present invention.
Figure 2:
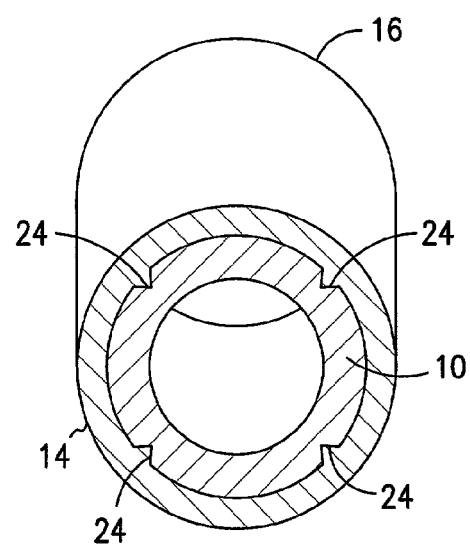
FIG. 2 is a sectional view of FIG. 1 taken at section 2—2.
Figure 3:
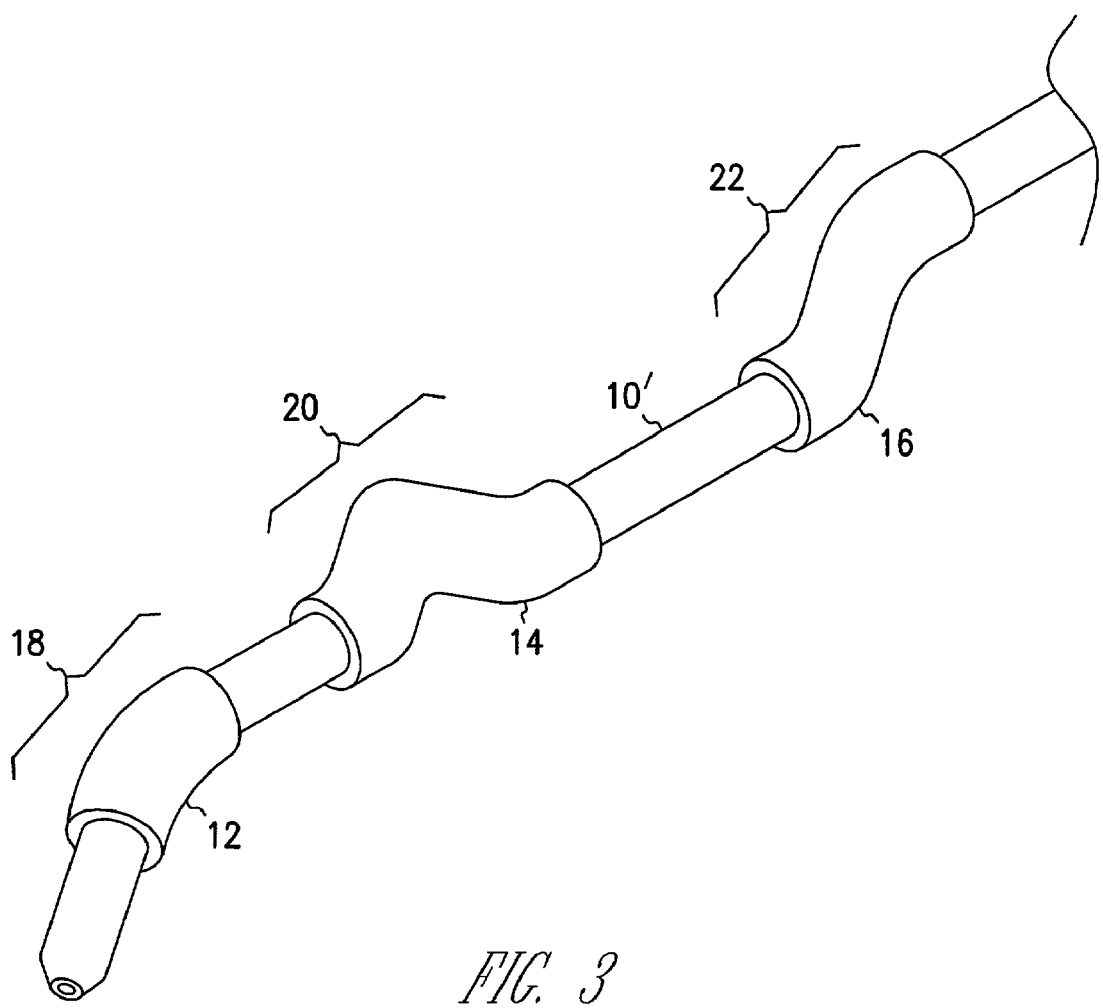
FIG. 3 is a pictorial view of a catheter fitted with three sleeves in accordance with the present invention.

In the drawings described below, reference numerals are generally repeated where identical elements appear in more than one figure. Turning now to the drawings, and in particular to FIGS. 1 and 2, there is shown a pictorial view of an exemplary implantable tubular device 10. The device 10 may be any of a number of different types of implantable tubular devices, such as a cardiac stimulator lead as shown in FIGS. 1 and 2, a catheter 10' as shown in FIG. 3, or other devices. The term "implantable" as used in this application should be understood to mean either long term implantation, as in the case of a drug infusion catheter, or to transient insertion into the body, as in the case of an endoscopic introducer. The implantable tubular device 10 is jacketed by three longitudinally spaced apart tubular sleeves 12, 14, and 16. Note that the sleeves 12, 14, and 16 are shown with an exaggerated diameter for clarity of illustration. In practice, the sleeves 12, 14, and 16 may be just slightly larger in diameter than the tubular device 10 so that the tubular device 10 retains an isodiametric character. The sleeves 12, 14, and 16 have been deformed to impart bends 18, 20, and 22 at preselected locations along the length of the tubular device 10. The sleeves 12, 14, and 16, are deformable by the implanting surgeon at or before the time of implantation of the tubular device 10 so that the surgeon may customize the shape of the tubular device 10 to readily adapt to the particular anatomical structures to be encountered by the device 10. The configuration of the tubular devices 10 and 10' shown in FIGS. 1, 2, and 3 are intended to be illustrative only. A skilled artisan will appreciate that the number and shapes of the sleeves may be varied to suit the particular anatomical structures anticipated. The following discussion of the sleeve 12 is illustrative of the sleeves 14 and 16.

Referring to FIGS. 1 and 2, the sleeve 12 may be secured to the implantable tubular device 10 and held in position by a variety of methods. If the sleeve 12 is provided with a longitudinally disposed slit 23 (as shown for the sleeve 16), the sleeve 12 may be spread apart and wrapped around the tubular device 10. If the inner diameter of the sleeve 12 is close enough to the outer diameter of the tubular device 10, the sleeve 12 may be held in place by interference. If the sleeve 12 is not provided with the slit 23, the sleeve 12 may be slipped over the tubular device 10 and advanced longitudinally until the sleeve 12 is positioned at the desired location. With or without an interference fit, the sleeve 12 may be secured with a biocompatible adhesive, such as, for example, Dow Medical Adhesive Silicone Type A, or similar adhesives, and/or via a plurality of barbs 24. The barbs 24 project radially inwardly from the interior surface of the sleeve 14 and penetrate slightly into the exterior surface of the implantable tubular device 10. The mechanism for securing the sleeves 12, 14, and 16 to the implantable tubular device 10 may encompass one, some, or all of the foregoing methods in combination.

The sleeve 12 is advantageously fabricated from a material that is capable of being readily deformed by the physician into a desired shape by hand or with the aid of simple tools, and thereafter hardened by exposure to a stimulus to retain the imparted shape. In this regard, the material may be a heat-sensitive shape-memory polymer or metal, or a polymer that may be deformed and subsequently hardened by chemical, photo, or thermal stimulation.

A heat-sensitive shape-memory polymer behaves generally like a rigid material while at temperatures below the glass transition temperature $T_g$, but undergoes significant softening and may be readily plastically deformed when heated above $T_g$. When the material is then cooled below $T_g$, the deformation is fixed and the shape remains stable. However, the original shape of the material may be recovered by reheating the material above $T_g$.

The glass transition temperature $T_g$ varies for different materials, and may vary for different batches of the same material depending on the processes used to make the batches of the material. In this regard, a material may be formed with a preselected $T_g$ that is tailored to a particular end use for the material. For materials utilized to make an implantable structure that is intended to retain a shape imparted by the surgeon, such as the sleeve 12, the appropriate $T_g$ should be above the anticipated maximum body temperature so that the structure does not soften and deform after implantation. Normal body temperature usually falls within the range 36 to 37° C. However, a body subjected to high fever may reach about 42° C., so a $T_g \geq 42°$ C. should ensure that the sleeve 12 does not soften appreciably after implantation.

In addition to exhibiting heat-sensitive shape-memory properties, the material selected for the sleeve 12 should be biocompatible. As the skilled artisan will appreciate, biocompatibility is more a matter of degree than an absolute. The requisite degree of biocompatibility for the sleeve 12 will depend on the anticipated duration of implantation for the tubular device 10. For tubular devices 10 intended for long-term implantation, such as certain types of shunts, drug infusion catheters, and endocardial leads, the sleeve 12 may be fabricated from heat-sensitive shape memory polymers such as polynorbornene supplied by Nippon Zeon of Japan, polyurethane supplied by Mitsubishi Heavy Industries of Japan, Calo.Mer™ supplied by Polymer Technology Group of California, or similar materials. If the tubular device 10 is designed for more transient implantation, such as an endoscopic introducer, materials such as polyvinyl chloride, or similar materials may be used in addition to the above-described materials. Metallic materials, such as, for example, Nitinol, or similar materials coated with biocompatible polymeric materials, such as polyurethane may also be used. Strength may be added to the sleeve 12 by mixing fibers, such as fiberglass, or similar materials, with the material forming the sleeve 12.

As noted above, the sleeve 12 may be alternatively composed of a polymer that may be deformed and subsequently hardened by chemical, photo, or thermal stimulation. For example, the sleeve 12 may be composed of a polymeric material that is compliant until exposed to an increase in pH, such as, for example, crosslinked collagen, or similar materials. A sleeve composed of such a pH sensitive polymeric material may be formed into the desired shape by the physician and then hardened by dipping the sleeve 12 into a higher pH solvent such as calcium chloride. Alternatively, the polymeric material selected for the sleeve 12 may be formulated to contain crosslinkable moieties so that the sleeve 12 may be hardened by photo or thermal stimulation. In this regard, the material for the sleeve 12 may be collagen, polylactic, or polyglycolic acid or combinations of these copolymerized with acrylic acid, or butadiene or other agents containing reactive double bonds. After deformation into the appropriate shape, light or heat energy would be applied to crosslink and harden the material.

Figure 4:
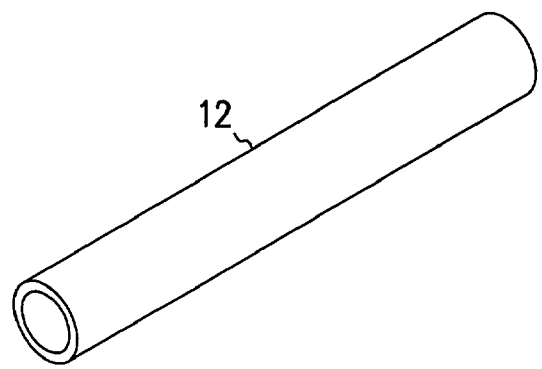
FIG. 4 is a pictorial view of an exemplary sleeve prior to thermal processing in accordance with the present invention.
Figure 5:
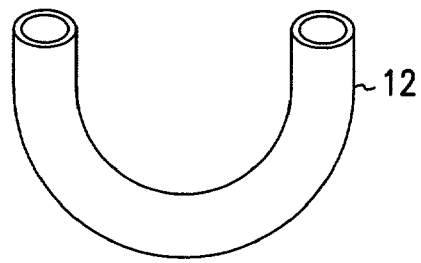
FIG. 5 is a pictorial view of the sleeve in FIG. 4 after thermal processing and deformation in accordance with the present invention.
Figure 6:
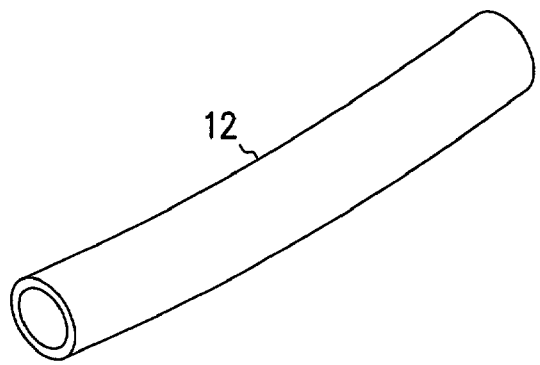
FIG. 6 is a pictorial view of the sleeve in FIG. 4 after reheating in accordance with the present invention.

The manner in which the sleeve 12 is deformed to impart the desired bends in the tubular device 10 will depend upon the material selected to make the sleeve 12. For a sleeve 12 fabricated from a heat-sensitive shape-memory material, the deformation process is illustrated in FIGS. 4, 5, and 6, which are pictorial views of the sleeve 12 at various stages of processing. FIG. 4 shows the sleeve 12 prior to deformation by the surgeon. The sleeve 12 is advantageously supplied with a straight original shape and is cut to a desired length by the surgeon. Prior to implantation of the tubular device 10 (See FIGS. 1–3), the sleeve 12 is heated above $T_g$ and deformed by the surgeon into the temporary shape shown in FIG. 5. The heating may be by hot bath, hot air, or some other method. The sleeve 12 is then cooled below $T_g$ and becomes rigid but retains the fixed bend shown in FIG. 5. The cooling may be by quenching, air cooling or some other method. If the initial shape is unsatisfactory, the sleeve may be reheated above $T_g$. When reheated, the sleeve 12 will normally recover almost completely to the original straight shape as shown in FIG. 6. The material chosen for the sleeve 12 may be selected to shrink in diameter upon heating. This property may facilitate the aforementioned interference fit to secure the sleeve 12 to the tubular device 10.

The deformation process for a sleeve 12 composed of a polymeric material that is permanently hardenable following chemical, photo, or thermal stimulation will generally follow the procedure described for a heat-sensitive shape-memory material. However, following the impartation of the temporary shape as shown in FIG. 5, the sleeve 12 will be permanently hardened by exposing the polymer to a hardening agent, such as a high pH solution, or to thermal or light energy.

A different deformation process may be used for a sleeve 12 composed of a memory metal, such as Nitinol, since the shape memory characteristics need not be utilized to establish the preselected shape in the implantable tubular device 10. In this regard, the shape memory character of the Nitinol may be used to fashion the sleeve 12 with an initial inner diameter slightly smaller than the anticipated outer diameter of the implantable tubular device 10. The sleeve 12 is then provided with an increased diameter by cold working to enable the physician to readily slip the sleeve 12 over the implantable tubular device 10. Subsequent application of heat by the physician will cause the sleeve 12 to return to its original smaller inner diameter thereby establishing a tight interference fit with the outer surface of the implantable tubular device 10. The sleeve 12 may then be readily deformed into the desired shape by the physician.

The sleeve 12 may be deformed prior to or after application to the tubular device 10. In the latter alternative, the sleeve 12 will be slipped over the implantable tubular device 10 and moved to the desired location along the length of the implantable tubular device 10. The sleeve 12 may then be deformed as described above.

Figure 7:
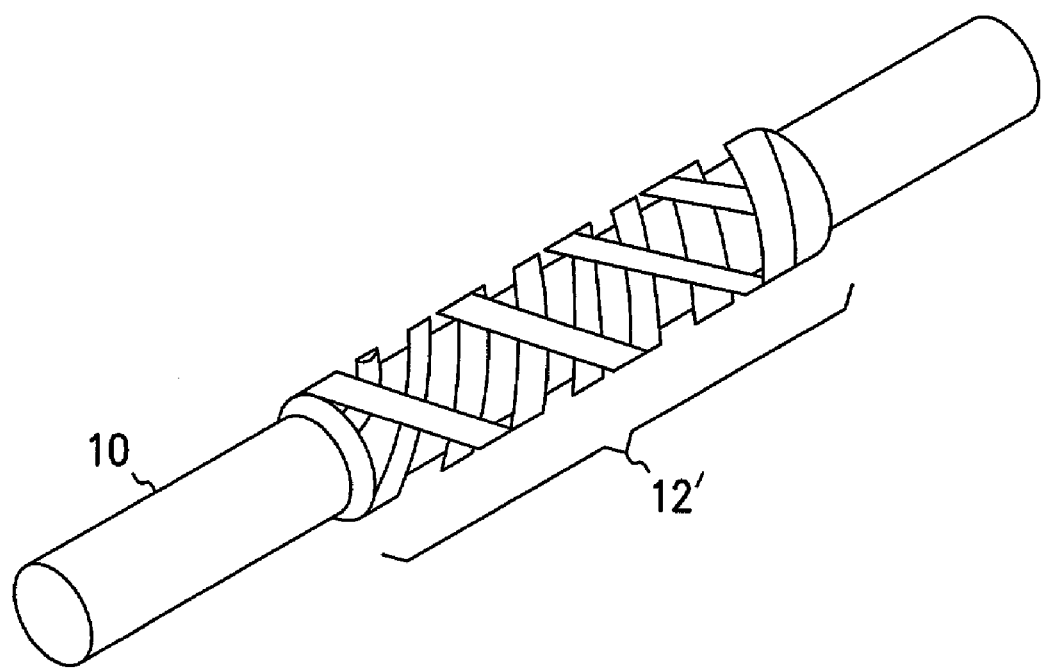
FIG. 7 is a pictorial view of an alternate embodiment of the sleeve incorporating a mesh configuration in accordance with the present invention.
Figure 8:
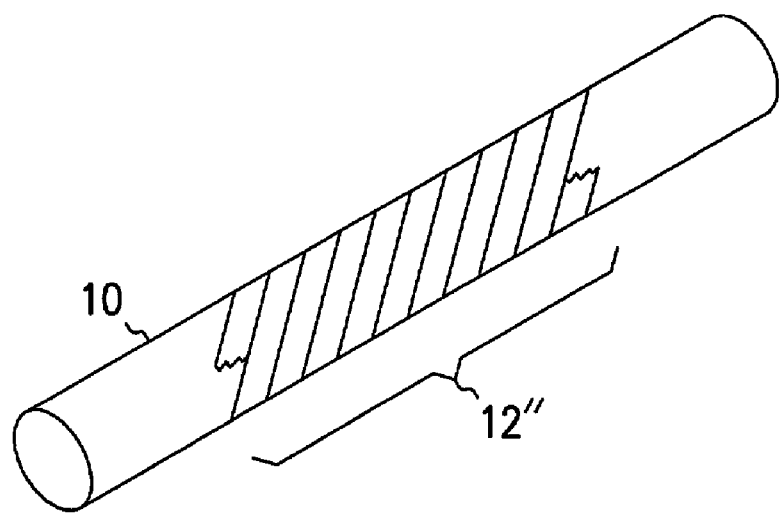
FIG. 8 is a pictorial view of an alternate embodiment of the sleeve incorporating a tape configuration in accordance with the present invention.

The sleeve 12 is depicted in FIGS. 1–6 as a unitary tubular structure. However, as shown in FIG. 7, the sleeve, now designated 12', may be alternatively fashioned from a woven fabric made from fibers of any of the aforementioned polymers. In another alternative shown in FIG. 8, the sleeve, now designated 12", may be manufactured in the form of a tape that is wrapped around the tubular device 10.

Figure 9:
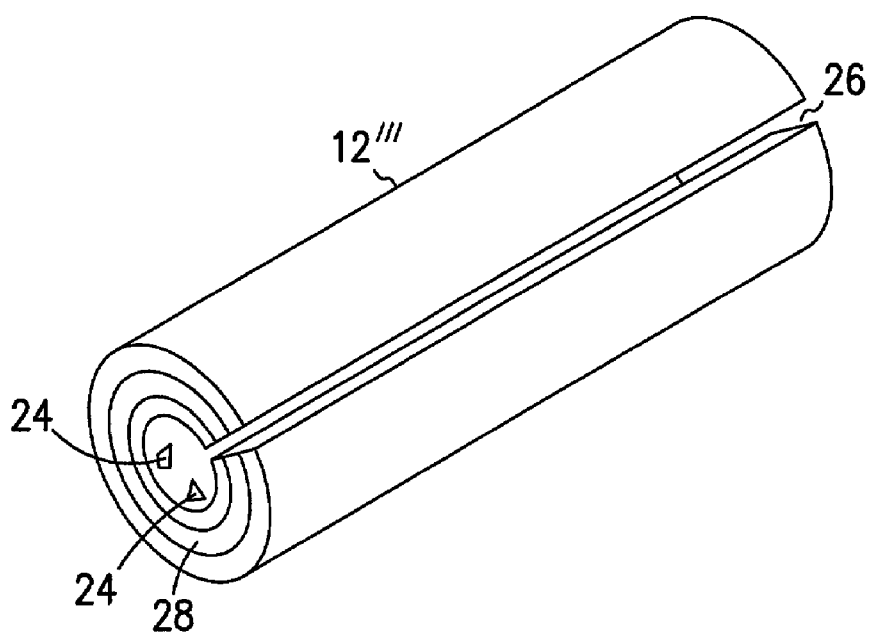
FIG. 9 is a pictorial view of an alternate embodiment of the sleeve incorporating a plastically deformable rib in accordance with the present invention.

In addition to relying on the deformation properties of the material used to fabricate the sleeve 12, structure may be incorporated into the sleeve 12 to enable the implanting surgeon to plastically deform the sleeve 12 into the desired shape. FIG. 9 is a pictorial view of the sleeve, now designated 12''', in an undeformed state and incorporating such structure. The sleeve 12''' is provided with a longitudinally disposed slit 26. The slit 26 enables the sleeve 12''' to be spread apart and wrapped over the tubular device 10, and aids in preventing the sleeve 12''' from crimping while being bent. To enable the sleeve 12''' to take on and hold a bend imparted by the surgeon, the sleeve 12''' is provided with an elongated rib 28. In the embodiment shown in FIG. 9, the rib 28 has the same general C-shaped cross section as the sleeve 12'''. The rib 28 is advantageously fabricated from a biocompatible material that may be plastically deformed comfortably by hand or with the aid of hand tools, such as, for example, MP35N alloy, titanium, stainless steel, or similar materials. The rib 28 may be secured to the sleeve 12''' by a suitable biocompatible adhesive or may be coupled to the sleeve at the time the sleeve 12''' is molded. The sleeve 12''' may be fabricated from the heat-sensitive shape-memory materials described above or from other biocompatible flexible materials, such as, for example, silicone rubber, polyurethane, or similar materials.

Figure 10:
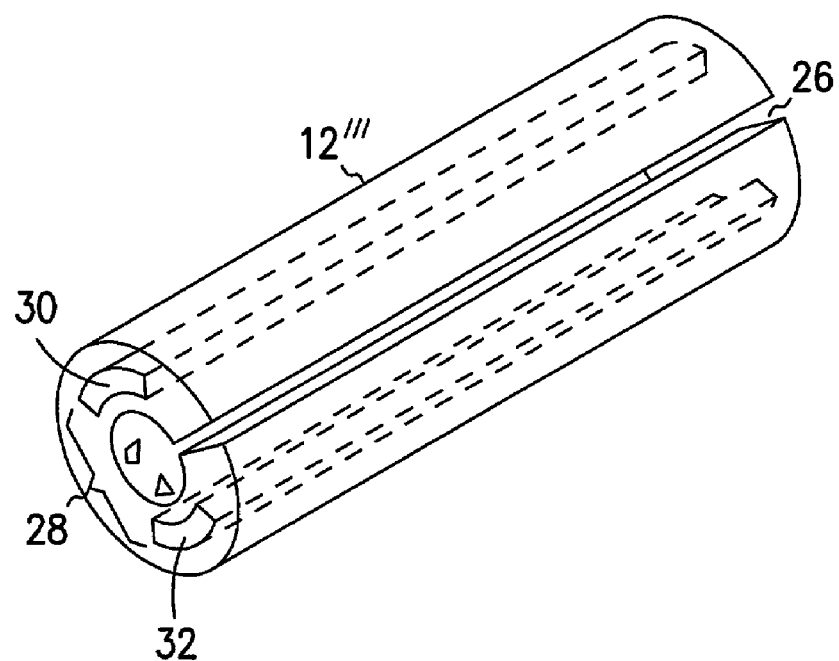
FIG. 10 is a pictorial view of an alternate embodiment of the sleeve incorporating two plastically deformable ribs in accordance with the present invention.
Figure 11:
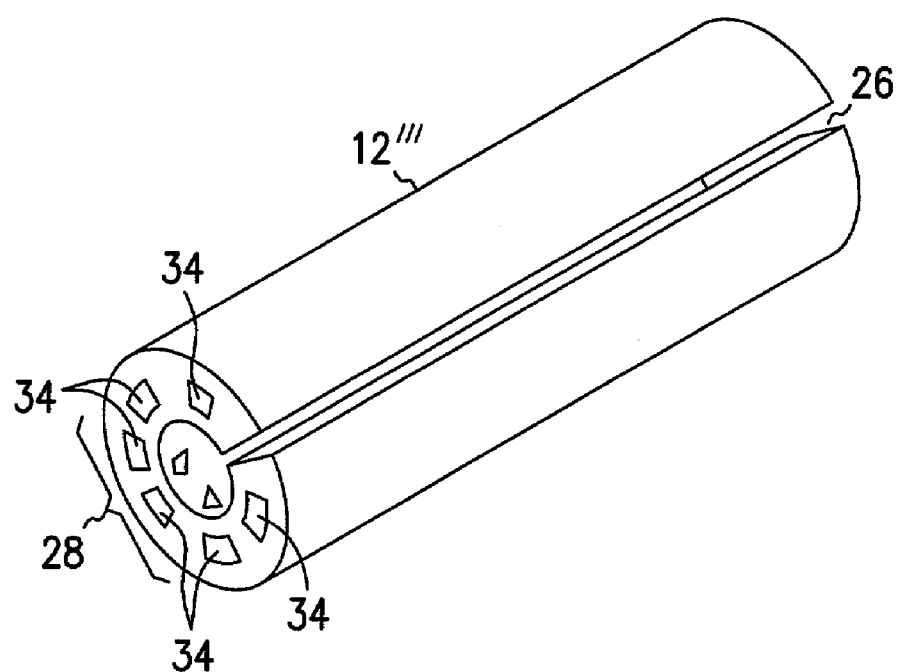
FIG. 11 is a pictorial view of an alternate embodiment of the sleeve incorporating a plurality of plastically deformable ribs in accordance with the present invention.
Figure 12:
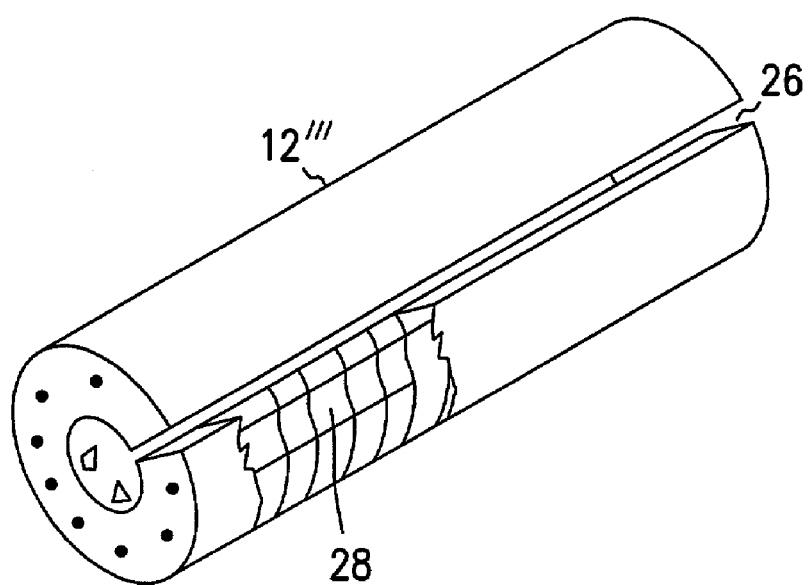
FIG. 12 is a pictorial view of an alternate embodiment of the sleeve incorporating a plastically deformable rib in the form of a tubular mesh in accordance with the present invention

As shown in FIGS. 10, 11, and 12, the rib 28 may take on a variety of different configurations. FIGS. 10, 11, and 12 are pictorial views of the sleeve 12''' showing these alternate arrangements for the rib 28. In FIG. 10, the rib 28 consists of two peripherally spaced elongated members 30 and 32, the bodies of which are shown in phantom. As shown in FIG. 11, the rib 28 may consist of a plurality of peripherally spaced elongated members, all designated 34, but not shown in phantom for simplicity of illustration. In FIG. 12, a portion of the exterior of the sleeve 12''' is shown cut away to reveal that the rib 28 may be configured as a tubular wire mesh.

Figure 13:
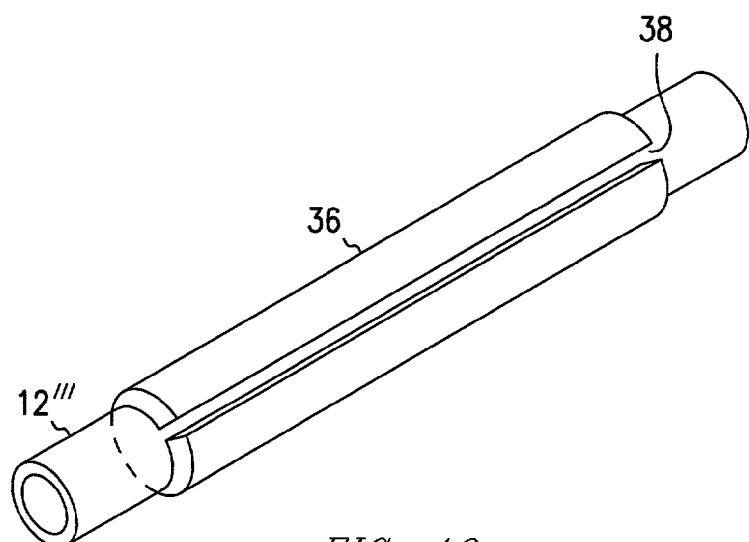
FIG. 13 is a pictorial view of the sleeve wrapped with a second sleeve prior to deformation in accordance with the present invention.
Figure 14:
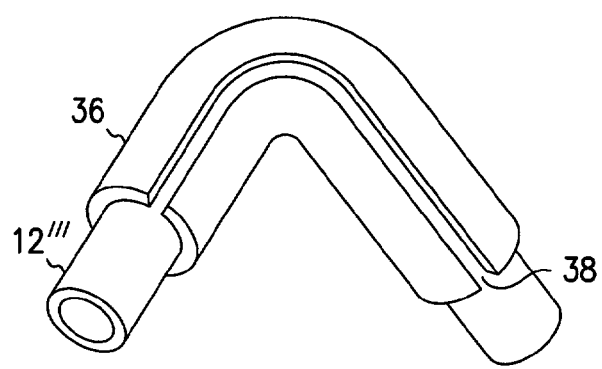
FIG. 14 is a pictorial view of the sleeve wrapped with a second sleeve after deformation in accordance with the present invention.
Figure 15:
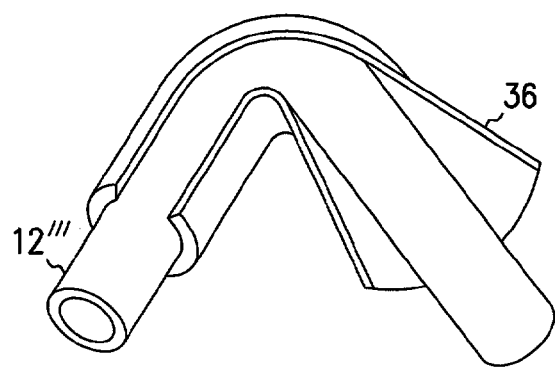
FIG. 15 is a pictorial view of the sleeve wrapped with a second sleeve showing removal of the second sleeve after deformation in accordance with the present invention.

The deformation of the sleeve 12''' may be understood by referring now to FIGS. 13, 14, and 15, which show, respectively, the sleeve 12''' before, during, and after the deformation step. The skilled artisan will appreciate that the deformation process should be undertaken in a way that avoids introducing crimps into the sleeve 12'''. In this regard, as shown in FIG. 13, the sleeve 12''' is fitted with a second or bending sleeve 36. The bending sleeve 36 is dimensioned to have an inner diameter that is just slightly larger than the outer diameter of the sleeve 12''' so that the bending sleeve 36 may be readily slipped over the sleeve 12'''. The bending sleeve 36 is provided with a longitudinally disposed slit 38 so that the bending sleeve 36 can be bent without crimping. The bending sleeve 36 is designed to protect the exterior of the sleeve 12''' and to prevent the sleeve 12''' from collapsing or crimping during the bending step. In this regard, the bending sleeve 36 is advantageously composed of a material that will plastically deform when bent by hand. Biocompatibility is not required, although the material should be sterilizeable.

As shown in FIG. 14, bending force is applied to the bending sleeve 36, which imparts the desired bend in the sleeve 12'''. The bending step may be performed in a variety of ways, such as, for example, by hand, or with the aid of tools such as tweezers, pliers, bending eaves, and the like and with or without the tubular devices in place. After the bending step shown in FIG. 14, the bending sleeve 36 should be removed as shown in FIG. 15. The bending sleeve 36 is removed by unwrapping as shown. Care should be exercised during this procedure to avoid damaging the sleeve 12'''.

Figure 16:
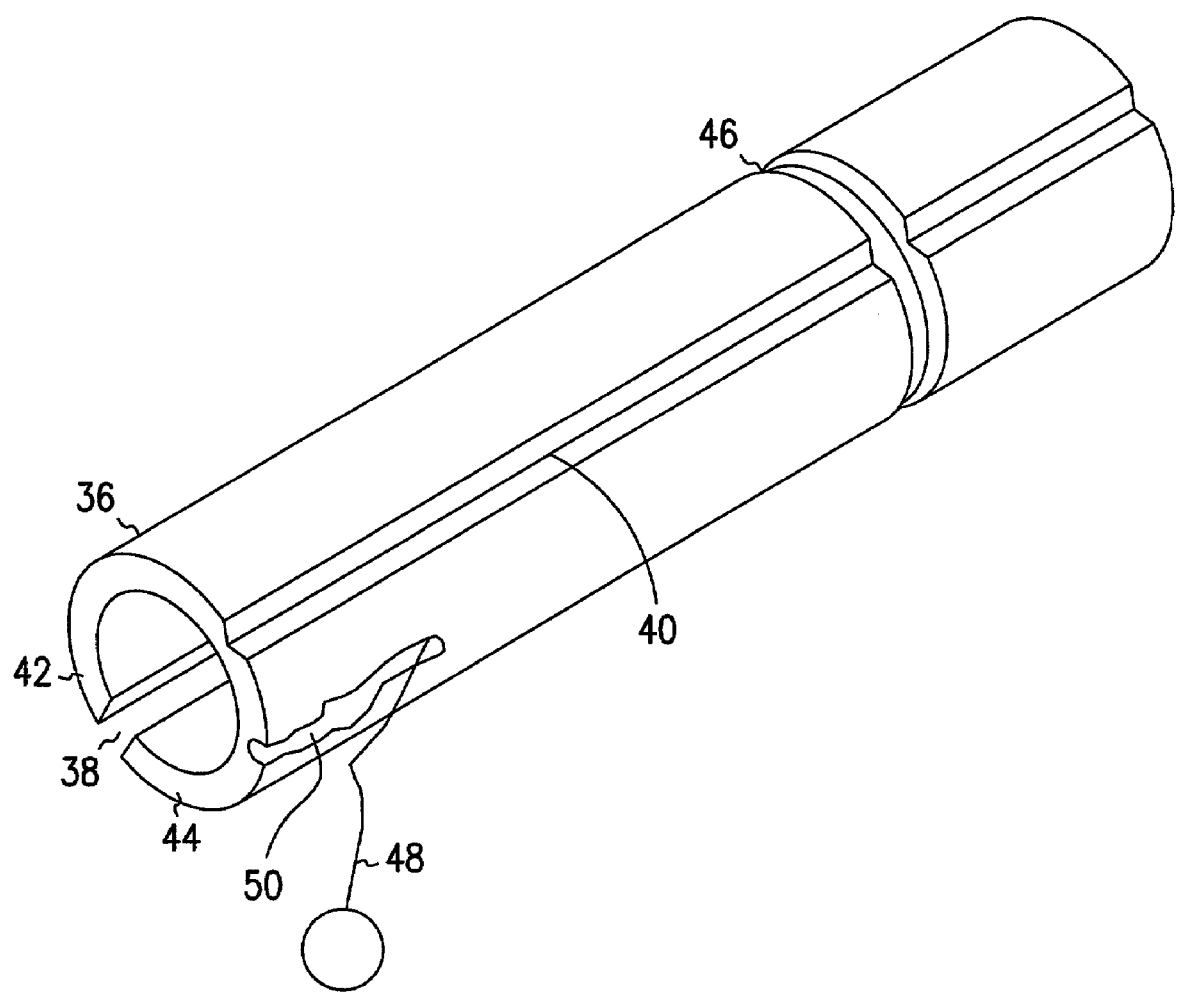
FIG. 16 is a pictorial view of an alternate embodiment of the second sleeve in accordance with the present invention.

Structure may be incorporated into the bending sleeve 36 that facilitates the quick removal thereof after the bending step. Referring now to FIG. 16, the bending sleeve 36 may be provided with one or more longitudinally disposed grooves 40. The groove 40 is formed in the exterior of the bending sleeve 36 to act as a stress riser so that when the opposing faces 42 and 44 of the sleeve are moved away from each other, the bending sleeve 36 will fracture along the groove 40. In this way, the bending sleeve 36 may be broken into two or more pieces and readily removed from the sleeve 12". In addition, one or more circumferentially disposed grooves 46 may be formed in the exterior of the bending sleeve 36 to provide further stress risers so that the bending sleeve may be readily broken into several small pieces and quickly removed. In addition, the bending sleeve 36 may be fitted with a rip cord 48 of the type routinely encountered in overnight delivery envelopes. The rip cord 48 is embedded in the bending sleeve 36 and longitudinally disposed so that when the rip cord 48 is pulled, a groove 50 is formed which provides a stress riser to facilitate fracture of the bending sleeve 36.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A method comprising:
  placing a first sleeve over an implantable tubular device;
  plastically deforming the first sleeve to a predetermined shape including imparting a bent shape to the first sleeve and the implantable tubular device, wherein deforming the first sleeve occurs at the time the implantable tubular device is implanted into a patient;
  placing a second sleeve over the sleeve prior to deforming the first sleeve; and
  retaining the first sleeve to an exterior surface of the implantable tubular device.

2. The method as recited in claim 1, wherein the first sleeve has a slit, and the method further comprises spreading apart the first sleeve and wrapping the first sleeve around the tubular device.

3. The method as recited in claim 1, wherein retaining the first sleeve to the exterior surface of the implantable tubular device includes securing the first sleeve to the tubular device with one or more barbs.

4. The method as recited in claim 1, wherein applying the first sleeve to an outer surface includes wrapping tape around the tubular device.

5. The method as recited in claim 1, further comprising providing the first sleeve with an elongate rib.

6. The method as recited in claim 1, further comprising providing the first sleeve with a rib having a C-shaped cross-section.

7. The method as recited in claim 1, further comprising providing the first sleeve with a rib having at least two peripherally spaced elongate members.

8. The method as recited in claim 1, wherein plastically deforming the first sleeve to a predetermined shape includes selectively deforming the first sleeve.

9. The method as recited in claim 8, wherein selectively deforming the first sleeve includes selectively deforming the first sleeve into a patient specific shape such that the bent shape imparted to the first sleeve and the implantable tubular device is specific to the shape requirements of the patient.

10. A method comprising:
  positioning a first sleeve over an implantable tubular device at a predetermined location;
  deforming and bending the first sleeve, wherein the first sleeve imparts a preselected bent shape in the implantable tubular device; and
  placing a second sleeve over the first sleeve and protecting the first sleeve while plastically deforming the first sleeve.

11. The method as recited in claim 10 wherein bending the first sleeve occurs at the time of implant.

12. The method as recited in claim 10, further comprising removing the second sleeve from the first sleeve.

13. The method as recited in claim 12, wherein removing the second sleeve occurs with manipulating structure incorporated into the second sleeve.

14. The method as recited in claim 12, wherein removing the second sleeve from the first sleeve includes pulling on a rip cord embedded within the second sleeve.

15. A method comprising:
positioning a first sleeve over an implantable tubular device at a predetermined location;
deforming and bending the first sleeve and establishing a preselected bent shape in the implantable tubular device;
placing a second sleeve over the first sleeve and protecting the first sleeve while plastically deforming the first sleeve; and
removing the second sleeve from the first sleeve including fracturing the second sleeve along a longitudinal groove in the second sleeve.

16. The method as recited in claim 15, wherein removing the second sleeve from the first sleeve includes separating the second sleeve into two or more pieces, and removing the pieces.

17. The method as recited in claim 15, wherein removing the second sleeve occurs with manipulating structure incorporated into the second sleeve.

18. A method comprising:
positioning a first sleeve over an implantable tubular device at a predetermined location;
deforming and bending the first sleeve and establishing a preselected bent shape in the implantable tubular device;
placing a second sleeve over the first sleeve and protecting the first sleeve while plastically deforming the first sleeve; and
separating the second sleeve into two or more pieces, and removing the pieces.

19. The method as recited in claim 18, wherein separating the second sleeve into two or more pieces includes separating the second sleeve along circumferentially disposed grooves in the second sleeve.

20. The method as recited in claim 18, wherein deforming and bending the first sleeve occurs at the time of implant.

21. A method comprising:
placing a plurality of sleeves over an exterior surface of an implantable tubular device, including spacing the plurality of sleeves longitudinally along the implantable tubular device;
plastically deforming each sleeve to a predetermined shape including imparting a bent shape to each sleeve and the implantable tubular device, wherein deforming the sleeve occurs at the time the implantable tubular device is implanted into a patient;
placing a second sleeve over at least one of the plurality of sleeves prior to deforming the plurality of sleeves; and
retaining each of the plurality of sleeves to the exterior surface of the implantable tubular device.

22. The method as recited in claim 21, wherein retaining each of the plurality of sleeves to the exterior surface of the implantable tubular device includes securing one or more of the plurality of sleeves to the tubular device with one or more inwardly facing barbs on the sleeves.

23. The method as recited in claim 21, wherein retaining each of the plurality of sleeves to the exterior surface includes retaining each sleeve with an interference fit.

24. The method as recited in claim 21 further comprising hardening each of the plurality of sleeves in its imparted shape including exposing each sleeve to a stimulus.

25. The method as recited in claim 24, wherein exposing each of the plurality of sleeves to the stimulus includes exposing at least one sleeve to a chemical stimulus.

26. The method as recited in claim 24, wherein exposing each of the plurality of sleeves to the stimulus includes exposing at least one sleeve to a photo stimulus.

27. The method as recited in claim 24, wherein exposing each of the plurality of sleeves to the stimulus includes exposing at least one sleeve to a thermal stimulus.

* * * * *